United States Patent [19]

Englehardt et al.

[11] Patent Number: 4,831,242

[45] Date of Patent: May 16, 1989

[54] CONTROL SYSTEM FOR HEALTH CLUB FACILITIES AND EQUIPMENT

[75] Inventors: William H. Englehardt, Wood Dale; Martin A. Keane, Arlington Hgts.; Olgerts J. Svilans, Chicago; Russell W. Krch, Justice, all of Ill.

[73] Assignee: Bally Manufacturing Corporation, Chicago, Ill.

[21] Appl. No.: 775,177

[22] Filed: Sep. 12, 1985

[51] Int. Cl.$^4$ .......................... G06F 15/21; G06K 5/00
[52] U.S. Cl. .................................... 235/382; 235/375;
235/382.5; 235/380; 340/825.31; 340/825.32;
364/401; 364/410; 177/25.19
[58] Field of Search ............... 235/419, 376, 377, 375,
235/382.5, 382, 381, 380; 340/825.31, 825.32,
825.24, 825.28, 323 R; 177/25.19; 364/400, 401,
402, 406, 410, 413, 415

[56] References Cited

U.S. PATENT DOCUMENTS

| | | | |
|---|---|---|---|
| 3,697,729 | 10/1972 | Edwards et al. | 235/381 |
| 3,719,927 | 3/1973 | Michels et al. | 340/825.31 |
| 3,725,650 | 4/1973 | Gelder | 364/402 |
| 4,103,150 | 7/1978 | von Ballmoos | 235/419 |
| 4,139,764 | 2/1979 | Petrini et al. | 340/323 R |
| 4,204,635 | 5/1980 | Hofmann et al. | 235/419 |
| 4,283,710 | 8/1981 | Genest et al. | 235/382.5 |
| 4,323,771 | 4/1982 | Chalker et al. | 235/377 |
| 4,366,873 | 1/1983 | Levy | 177/25.19 |
| 4,423,792 | 1/1984 | Cowan | 177/25.19 |
| 4,567,359 | 1/1986 | Lockwood | 235/381 |
| 4,575,622 | 3/1986 | Pellegrini | 235/382 |
| 4,576,244 | 3/1986 | Zeigner et al. | 177/25.19 |

Primary Examiner—Alan Faber
Assistant Examiner—Robert A. Weinhardt
Attorney, Agent, or Firm—Jenner & Block

[57] ABSTRACT

A control system for a health club which stores user records including user activity data in order to monitor and control use of the club's facilities. A central controller includes a memory for storing the user records including attendance data and accounting data, and a main control which is responsive to the user record data for determining whether a user is authorized to use the club's facilities. The central controller is coupled to various club facilities and equipment such as a computerized scale to prevent use thereof if a user is not authorized. The central controller also stores user history data such as user weight data for the computerized scale to alleviate data storage problems.

19 Claims, 4 Drawing Sheets

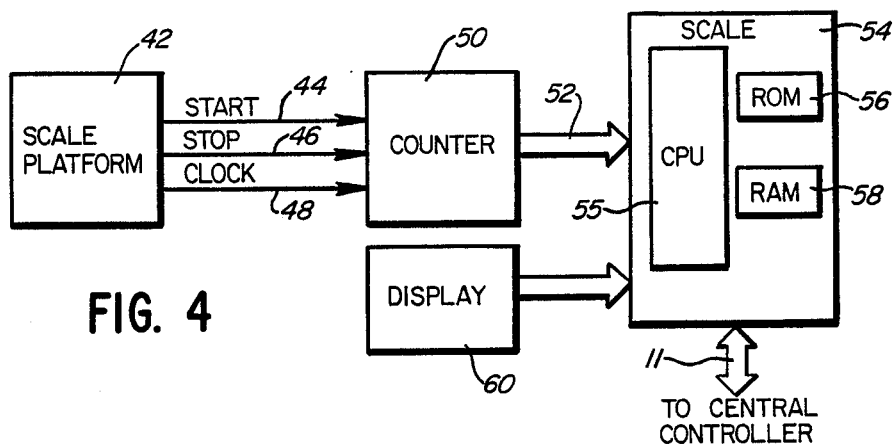
FIG. 4
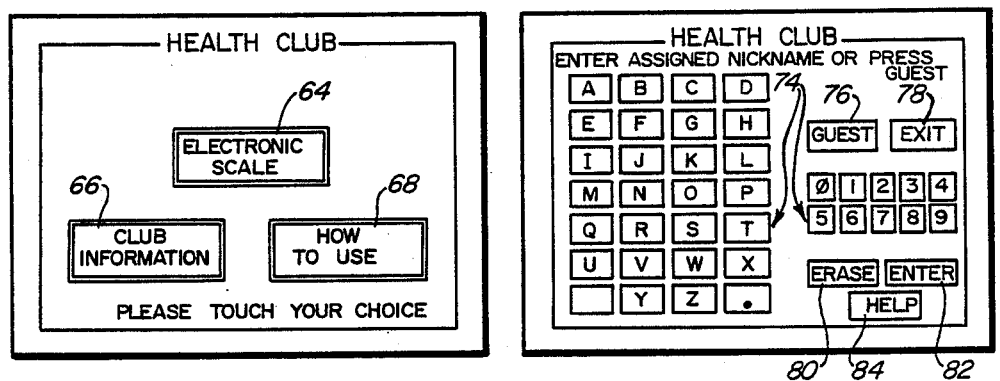
FIG. 6
FIG. 7
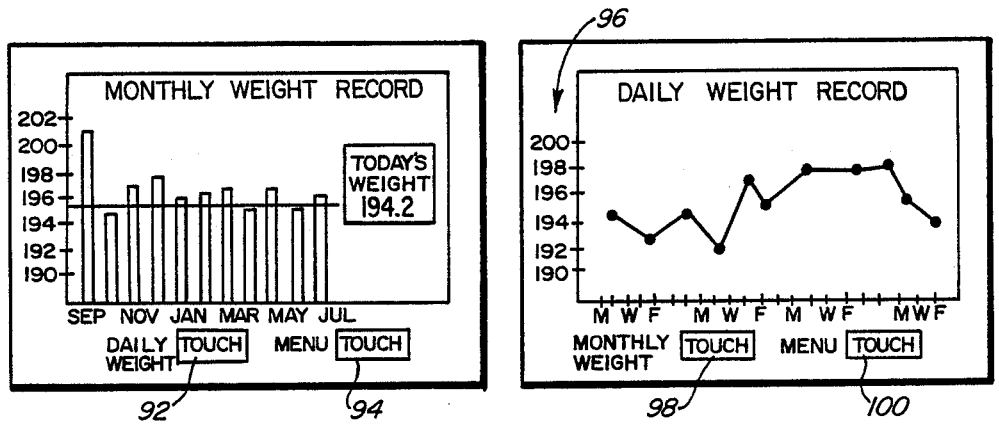
FIG. 8
FIG. 9

CONTROL SYSTEM FOR HEALTH CLUB FACILITIES AND EQUIPMENT

TECHNICAL FIELD

The present invention relates to a for a health club having facilities which include user equipment and more particularly to a health club control system which stores user records including user activity data in order to monitor and control use of the club's facilities.

BACKGROUND OF THE INVENTION

The public's concern over health and fitness has increased dramatically in recent years. Health clubs have been formed in order to provide a pleasant environment in which to exercise and to provide various incentives to help members stay fit. With booming memberships, health clubs have had problems in monitoring and controlling the use of their facilities to ensure that they are used only by authorized users. Typically, club members are provided with a membership card. To gain access to the club facilities, the card is usually shown to an attendant at a check-in desk who merely looks to see that it is a proper card for the club. Heretofore, from a visual inspection of the card, the attendant has had no way of knowing whether the user is current in paying his or her membership dues or whether the user is in fact the real owner of the card.

Large club memberships cause further problems to health clubs which have computerized equipment such as scales or exercise machines. Often such computerized equipment requires user records to be stored to provide a history of various physical attributes of the user. The history data may then be used to provide an indication of the user's progress. For example, computerized scales are known which display the weight history of a user as well as his current weight. Such equipment, however, typically does not have the capability necessary to store user history information for clubs with large memberships. Further, when a health club has plural computerized machines or scales, each machine or scale must store the same user history information. The cost for providing and maintaining such equipment with duplicate memories, however, is prohibitive.

SUMMARY OF THE INVENTION

In accordance with the present invention, the problems of unauthorized club facility access and user record storage of prior health club facilities have been overcome. The health club control system of the present invention includes a central controller which stores and monitors user records so that only authorized club members or guests may use the club's facilities. The central controller is further coupled to the club's computerized equipment so as to provide user records thereto in order to alleviate the equipment's storage problems.

The central controller includes a memory for storing user record data such as attendance data, accounting data, weight data, etc. The central controller also includes a main control which is responsive to the user record data stored in the memory for determining whether a user is authorized to use the club or not. The central controller is coupled to health club equipment, each piece of equipment having an input device which is controlled by an equipment user for identifying the user. The equipment also includes an equipment control for controlling its operation. In order to use the equipment, a user first enters his identification on the equipment input device. The equipment control then transmits the identification to the main control of the central controller. The main control determines whether the user is authorized from the user record data stored therein and if the user is authorized, the central controller signals the equipment control to permit use of the equipment. If the user is not authorized as determined by the main control, the equipment control prevents use of the equipment.

In one embodiment of the present invention, the central controller is coupled to a computerized scale to facilitate storage of user data employed by the scale and to monitor the scale's use so that only members of the club in good standing and authorized guests may use the scale.

The system further includes means coupled to the central controller for checking a user into the club. The check-in means has an input device which is used to identify a club user. This input device may include a card reader for reading a club membership card having user identification information encoded thereon. The check-in means further includes a display which is coupled to the main control to provide the status of the user i.e. whether he is authorized, not authorized or suspicious and to provide selected user records.

These and other objects and advantages of the invention as well as the details of an illustrative embodiment will be more fully understood from the following description and the drawings.

BRIEF DESCRIPTION OF THE DRAWINGS

FIG. 4 is a block diagram of the computerized scale of FIG. 3;

FIG. 6 is a view of a graphic presentation displayed at the scale illustrating the main menu;

FIG. 7 is a view of a graphic presentation displayed at the scale illustrating a touch screen keyboard;

FIG. 8 is a view of a graphic presentation displayed at the scale illustrating a monthly weight graph; and FIG. 9 is a view of a graphic presentation displayed played at the scale illustrating a daily weight graph.

BEST MODE FOR CARRYING OUT THE INVENTION

Figure 1:
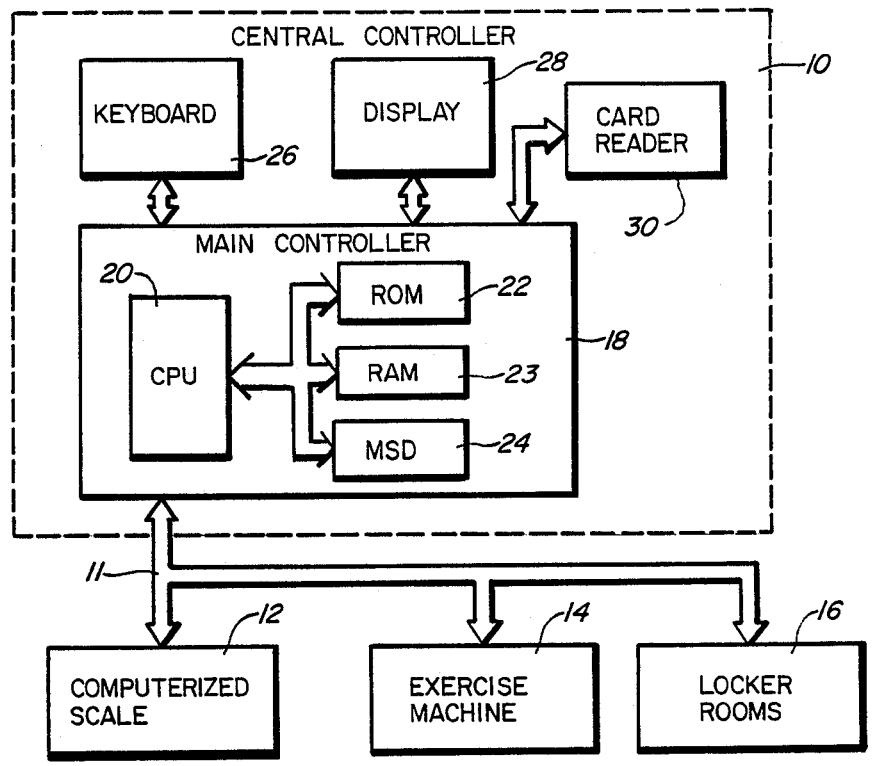
FIG. 1 is a block diagram of the health club control system of the present invention.

As shown in FIG. 1, the health club control system of the present invention includes a central controller 10 which is coupled by a bus 11 to the health club's facilities and user equipment such as a computerized scale 12, exercise machine 14 and the doors of the club's locker rooms 16. The central controller 10 monitors these health club facilities to ensure that they are used only by those who are authorized such as club members who are in good standing or checked-in guests and further stores user record data for the facilities to alleviate storage problems.

The central controller 10 includes a main control 18 having a central processing unit 20 which operates according to programs stored in a ROM 22 and a RAM 23. The main control also includes a mass storage device, MSD, 24 for storing programs, user record data such as club attendance data and accounting data as well as data representing the user's various activities in the club. The user activity data stored in the MSD 24 may include history data, for example, such as the weight of a user over a period of time or data reflecting other physical attributes of a user which might be measured by the health club equipment. The central controller 10 also includes a keyboard 26, a display 28 and card reader 30 which are each coupled to the main control and which may be disposed at a club check-in station operated by a club attendant.

The check-in station at the health club may be used to enroll new members, to authorize guests and to check whether card carrying users are authorized to use the club, i.e. whether the users are members in good standing. In order to enroll a new member, the check-in station attendant merely enters the enrollment data on the keyboard 26 from which it is transmitted to the main control 18 and stored as user record data in the MSD 24 under the control of the CPU 20. Similarly, in order to authorize a guest to use the club facilities, the attendant enters guest data on the keyboard 26 to set up a temporary guest user record data file in the MSD 24. The temporary guest user file stored in the MSD 24 is used by the club's equipment such as the scale 12 to allow the guest to use the equipment as described in detail below. In order to check a card carrying user into the club, the attendant at the check-in station may enter the user's name or identification number into the main control 18 by means of the keyboard 26. Alternatively, a membership card which is encoded with the user's identification information may be used with a card reader 30 to transmit the encoded identification data to the main control 18. In response to the user identification information, the main control 18 checks the user's record data stored in the MSD 24 to determine whether the user is authorized or not and provides a check-in presentation on the display 28 as shown in FIG. 2.

The record data shown on the display 28 may include an area 32 to show the user's name, address and description such as sex, height and weight. An area 34 of the display is provided for enrollment data such as the date that the user's membership started, the date through which the user has paid for his membership and the user's renewal fee. Attendance data is shown in the area 36 of the display and includes a list of each day that the user has attended the club over a given period of time. A card section 38 of the display shows information as to the number of people who are authorized to use the member's card such as a spouse or a child. A user's status indication 40 is provided on the display to indicate whether the user is authorized to use the club, not authorized or suspicious. The section 40 may be color coded to readily indicate to the check-in attendant the status of the user. The status indication section 40 may also include a message such as the word "valid" to indicate that the user is authorized.

Figure 2:
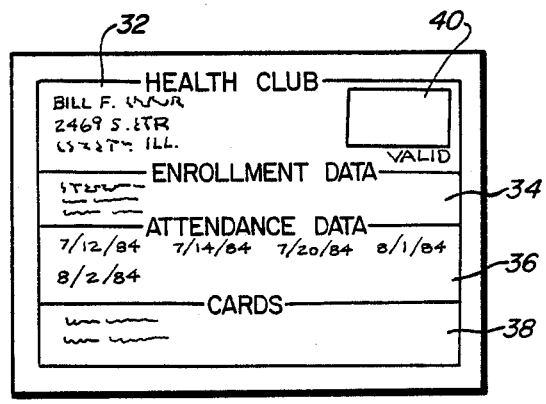
FIG. 2 is a view of a graphic presentation displayed at the health club's check-in station.

The check-in display format as shown in FIG. 2 allows the attendant to check the status of a club card user in seconds. The user will be authorized by section 40 if he or she is a paid up member in good standing as of that day. The user will be indicated as unauthorized by section 40 if he or she is not a paid up member. A user will be indicated as suspicious by the status section 40 if, for example, the main controller 18 determines that the user has attended the club an unlikely number of times within a fixed period of time. For example if the user has attended the club twice in one day or six days in one week, which is unlikely, a warning will be provided by section 40 to indicate to the attendant that a further investigation should be made before authorizing this user. If a warning indication is provided by section 40, the attendant need merely look at the club member's description in section 32, which specifies the user's sex, height and weight to determine whether the user is the real membership owner or someone who is posing as the owner. If the attendant determines that the user is the real membership owner, he may authorize the user by signalling the main control 18 by means of the keyboard 26. The warning indication provided by section 40 is extremely helpful in monitoring use of the club's facilities to ensure that they are used only by authorized users.

Figure 3:
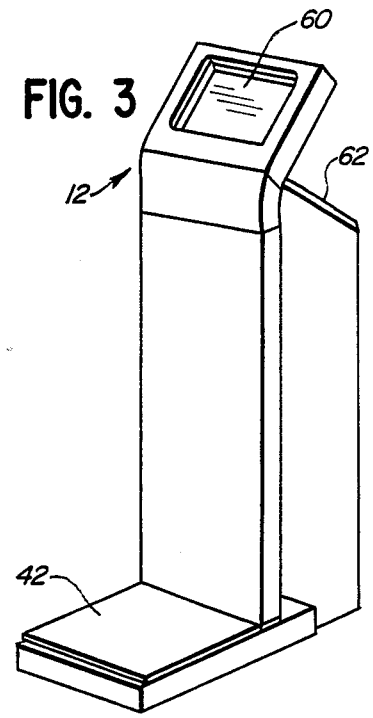
FIG. 3 is a perspective view of a computerized scale employed in the control system of the present invention.
Figure 5:
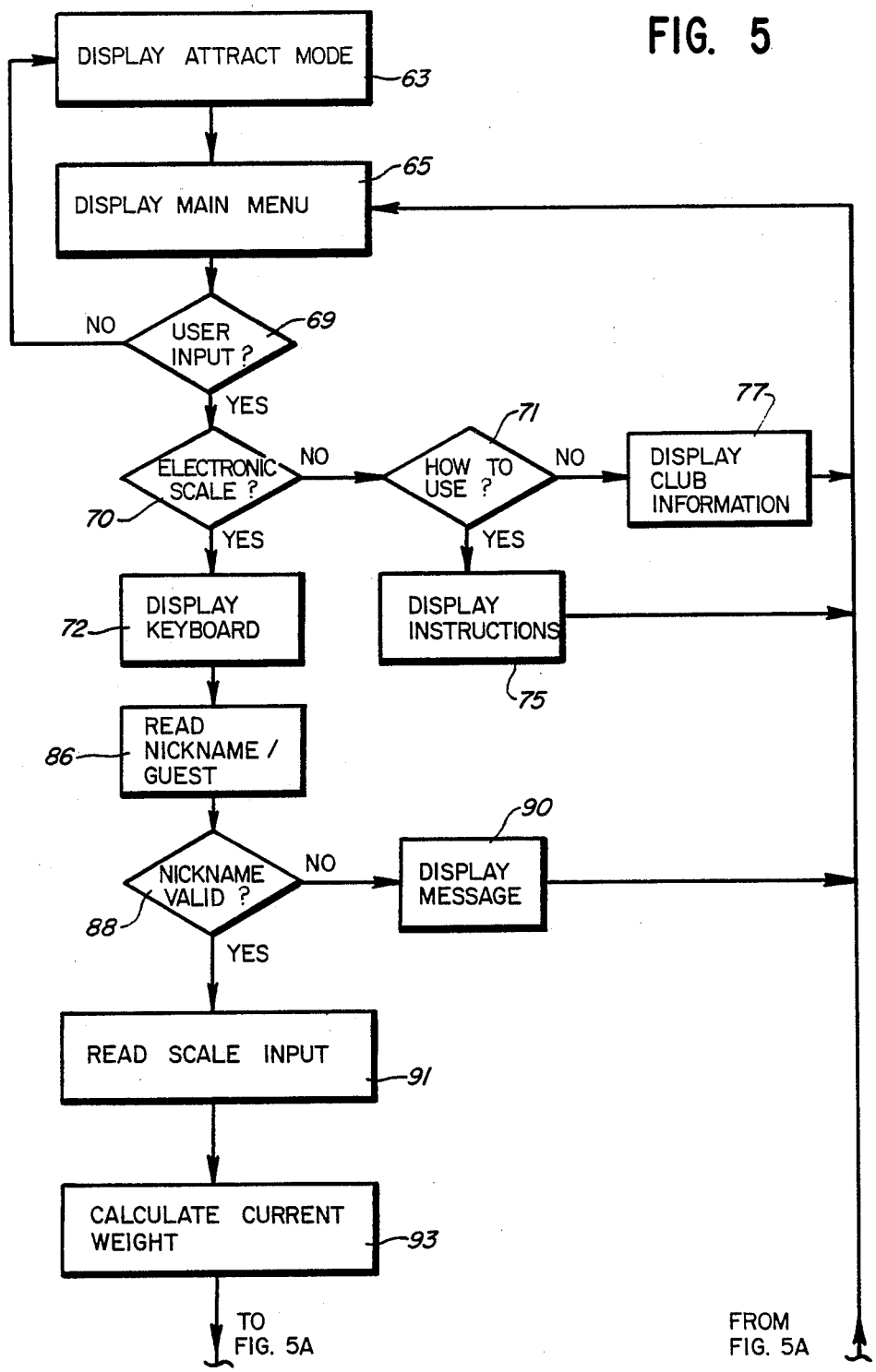
FIGS. 5–5A is a flow chart illustrating the computerized scale operations.
Figure 5A:
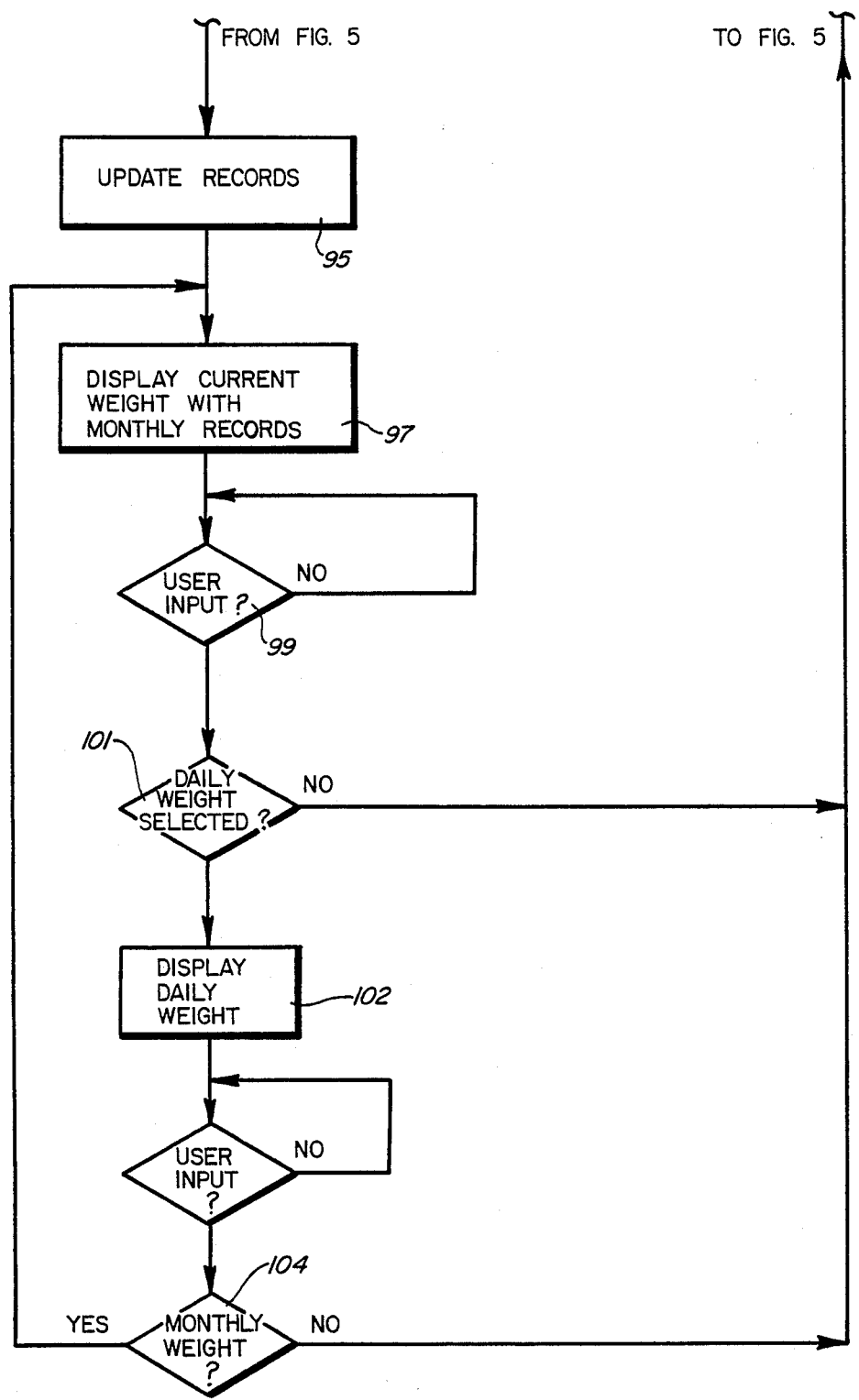

The computerized scale 12 which is coupled to the central controller 10 is shown in FIG. 3. The scale 12 includes a platform 42 on which a user stands to have his weight measured. The platform 42 may be formed of any standard scale which, as shown in FIG. 4, provides start and stop signals 44 and 46 and a clocked pulse train output 48, the number of pulses of which are proportional to the user's weight. A counter 50 is responsive to the scale outputs 44, 46 and 48 to provide a four digit BCD number on bus 52 to a scale microprocessor 54. The scale processor 54 includes a CPU 55 which operates according to the programs stored in a ROM 56 and a RAM 58 to determine the user's weight and to control a display 60. The microprocessor 54 also uses the RAM 58 for storing data transmitted to the scale from the central controller 10 and for providing scratch pad memory. The counter 50 and scale microprocessor 54 as well as the interface circuits necessary to communicate with the central controller 10 are disposed in the housing 62 in the rear of the scale 12. The display 60 is positioned a distance above the scale platform 42 to facilitate viewing by a user. The display 60 may be a touch screen so as to provide a non-intimidating means for the user to enter information to the scale processor 54 or the scale may be provided with a separate input keyboard or voice recognition system to be operated by the scale user.

The operation of the scale will now be described with reference to FIGS. 5-9. When the scale 12 is not in use, the processor 54, at step 63 controls the touch screen display 60 to show a graphic presentation to entice passersby to use the scale 12. When a user touches a main menu touch section, displayed on the screen 60 during the graphic presentation, the processor 54 displays a main menu on the touch screen as illustrated in FIG. 6. The main menu of the touch screen includes three touch sections, an electronic scale section 64, a club information section 66 and a how to use section 68. In order to select one of these three choices, the user merely touches the display screen 60 at the menu section of his choice. If the processor 54 determines that the user has stepped off the scale at block 69, the attract mode is displayed again at step 63. If the user has selected a main menu choice, the processor determines whether the electronic scale was selected at block 70. If the electronic scale was not selected but the how to use section 68 was, as determined at block 71, the processor 54, at block 75 displays instructions to the user. The main menu is then displayed again at block 65. If the club information section 66 is selected, the processor 54, at block 77, displays the information which may include dates of upcoming events etc.

If the electronic scale was selected from the main menu as determined at block 70, the processor 54, at block 72, displays a touch screen keyboard as illustrated in FIG. 7. The keyboard includes touch sections representing alpha numerics as shown at 74. Touch sections for a guest 76, exit 78, erase 80, enter 82 and help 84 are also provided on the display. In order to use the scale, the user must enter his nickname or the identification number associated with his user records stored in MSD 24 by means of the touch screen keyboard. If the user is a guest, the system may be set up to allow the guest to have immediate access to the scale such that the guest's weight is shown on the display 60 in response to touching the guest touch section 76. Alternatively, the system may require that the guest first check-in at the check-in station so as to set up guest user record data in the central controller's MSD 24. In this case a guest will be authorized to use the scale only if he has first checked-in.

When the user enters his nickname or other appropriate identification information through the touch screen sections 74 and 82, the processor 54 reads the information at block 86 and transmits it to the main control 18. In response to the identification information, the main control determines whether the user is an authorized member or guest at block 88. If the user is not authorized as determined at block 88, the processor 54 at block 90 displays a message to that effect on the screen 60. The processor 54 prevents use of the scale by the unauthorized user by returning to step 65 to display the main menu as opposed to displaying the user's weight.

If the user is an authorized member as determined by the main control 18, the main control transmits the user's official name, member number, and user record data including the user's weight and time history data to the processor 54. In response thereto, the processor 54, reads the weight signal from the counter 50 at step 91 and at step 93 calculates the user's current weight. After calculating the user's current weight, the processor 54 transmits the current weight with the user's member number back to the main control 18 so that the main control may update its user record data stored in the MSD 24 at block 95.

The user's current weight is displayed at block 97 with the user's monthly weight records as illustrated in FIG. 8. The user's monthly weight records may be presented in bar graph form as shown. The monthly weight display further includes two touch sections 92 and 94 which require a user input, the section 92 representing a daily weight display request and the section 94 representing a main menu display request. If the user selects one of the displays by touching the screen sections 92 or 94 as determined by block 99, the processor 54 next determines at block 101 whether the daily weight display section 92 was touched. If the user selects the daily weight display, the processor 54 controls the display at block 103 to show a line graph representing the user's weight for each day he was weighed on the scale over the past month. The range of the user's weight shown at 96 on the display, varies depending on the user's weight history so that the line graph is centered in the middle of the display. The daily weight display further includes two touch sections 98 and 100 respectfully representing the monthly weight display and the main menu display. If the monthly weight display touch section 98 is actuated by the user as determined at block 104, block 97 is returned to by the processor 54 to display the user's monthly weight history. If the main menu touch section 100 is actuated by the user, the processor returns to step 65 to display the main menu.

If the user is an authorized guest, having checked into the club, instead of transmitting user history data to the scale to provide the graphic presentations at blocks 97 and 103, the main control 18 may transmit data to the scale to provide a comparison between the guest's weight and the weight of club members of the same sex and age. The comparison data may be shown on the display in any suitable format.

A number of computerized scales may be coupled to the central controller 10 in order to use the data stored in the controller's MSD 24 so that duplicate user record data need not be stored at each scale. Because the scale itself does not store the user data, the scale can accommodate a larger number of users than has heretofore been possible.

Further, the central controller 10 monitors the computerized scale 12 so that only authorized members and guests may use it. Guests are easily accommodated by the system and may be automatically authorized to use the scale. Alternatively, records for a guest may be set up at the check-in station for use by the scale. The records set up for a guest at the check-in station may include the sex and age of the guest to allow a display showing the guest's weight as compared to other club users of the same sex and age. Other comparison presentations may be provided on the display 60 for guests as well as club members. The information necessary to make the comparison need only be stored in the central controller's MSD 24 where it may be accessed by the scale's processor 54 for display on the touch screen 60.

I claim:

1. For use in a health club having facilities including user equipment, a control system for monitoring use of the club facilities comprising:
   input means for accepting input data including data identifying a club facility user, user personal data, user accounting data and user activity data;
   memory means for storing user records including said user data;
   main control means responsive to the input means and the user records stored in said memory means for checking said user personal data, said user accounting data and said user activity data stored in said user records corresponding with data identifying a user received from said input means to determine whether the user is authorized to use the club facilities; and
   means responsive to the main control means for preventing use of club facilities if the main control means determines that the user is unauthorized.

2. The system of claim 1 wherein said user equipment includes a scale, the control system being coupled to the scale to prevent use of the scale by an unauthorized user.

3. The system of claim 1 wherein said user equipment includes an exercise machine, the control system being coupled to the exercise machine to prevent use of the machine by an unauthorized user.

4. The system of claim 1 wherein said club facilities include a locker room having a door through which access to the room is gained, the control system being coupled to the door to prevent use of the locker room by an unauthorized user.

5. The system of claim 1 wherein said main control means including account determining means responsive to said accounting data for determining whether the user is a paid-up member of the club, a user being authorized if the user is a paid-up member.

6. The system of claim 5 further including means for creating guest record data for non-club members, said main control means being responsive to said guest record data for determining whether the guest is authorized to use the club facilities.

7. For use in a health club, a control system for monitoring user activity comprising:
input means for accepting input data including data identifying a club user, user personal data, user attendance data and user accounting data;
memory means for storing in user records said input data;
means responsive to said input data for displaying said data stored in said user records;
main control means operatively connected to said memory means and responsive to the input means and said input data for checking said user personal data, said user accounting data and said user activity data stored in said user records corresponding with data identifying a user received from said input means to determine whether a user is authorized, not authorized or suspicious wherein said suspicious determination is based on predetermined user attendance criteria, said main control means being coupled to the display means to provide a display of said determination.

8. The system of claim 7 wherein the main control means determines a user to be suspicious in response to attendance data showing that the user has used the club a predetermined number of times within a predetermined period of time.

9. The system of claim 8 wherein said display means, in response to a determination that a user is suspicious, displays a warning indication and attendance data for the suspicious user.

10. For use in a health club, a control system for a scale to provide weight histories of plural users comprising:
a central controller including:
memory means for storing record data including weight and time data for a plurality of users, user attendance data and user accounting data; and
main control means responsive to the user record data for determining whether a user is authorized to use the scale, the scale including:
input and display means controlled by a user for inputting a user identification and for displaying information to the user;
means for transferring the user identification from the input means to the central controller, said central controller being responsive to the user identification to determine from the user's record data including said user accounting data and said activity data stored in said memory means whether the user is authorized and to transfer said user weight and time data to the scale on the transferring means if said user is authorized;
means for providing a signal representative of the current weight of a user; and
scale control means responsive to the user weight and time data transferred to the scale from the central controller and to the current weight signal for controlling the input and display means to display the user's weight history.

11. The control system of claim 10 wherein said input and display means displays the data in a line graph format.

12. The control system of claim 10 wherein said input and display means displays the data in a bar graph format.

13. The control system of claim 10 wherein the main memory further stores club information which can be selectively displayed on the input and display means.

14. The control system of claim 10 wherein a user is authorized if the user's record data shows that the user is a member of the club in good standing, the system further including means for setting up record data for a guest who is a non-club member to enable the guest to be an authorized user.

15. For use in a health club, a control system for monitoring user activity comprising:
a central controller including memory means for storing user identification and user data for a plurality of users; and
a plurality of health club equipment coupled to the central controller each of said equipment including:
input means controlled by an equipment user for identifying the user;
means responsive to the input means and coupled to the main control means for the central controller for transmitting to central controller the identity of the equipment user and user data generated by said health club equipment to said memory means and receiving from said memory means said user data stored in said memory means for said equipment user; and
means operatively connected to said transmitting means for controlling the operation of the equipment.

16. The system of claim 15 wherein the main control means includes means for transferring user data from the memory means to the equipment control means in response to a determination that the equipment user is authorized.

17. The system of claim 16 wherein said equipment is a scale having a display controlled by the equipment control means and the user data includes data representing the weight history of the user which is transferred to the equipment control means to be shown on the display.

18. The system of claim 15 wherein the equipment input means includes means for displaying messages to the user in response to a user input.

19. The system of claim 15 wherein said equipment is exercise equipment.

* * * * *